(12) United States Patent
O'Lenick, Jr.

(10) Patent No.: US 6,175,028 B1
(45) Date of Patent: Jan. 16, 2001

(54) SILICONE ALKYL PHOSPHATE ESTERS

(76) Inventor: Anthony J. O'Lenick, Jr., 2170 Luke Edwards Rd., Dacula, GA (US) 30019

(*) Notice: Under 35 U.S.C. 154(b), the term of this patent shall be extended for 0 days.

(21) Appl. No.: 09/513,900

(22) Filed: Feb. 28, 2000

(51) Int. Cl.$^7$ .................................................... C07F 7/08
(52) U.S. Cl. ............................................. 556/405; 528/25
(58) Field of Search ............................... 556/405; 528/25

(56) References Cited

U.S. PATENT DOCUMENTS

| | | | | |
|---|---|---|---|---|
| 3,849,462 | * | 11/1974 | Lengnick | 556/405 |
| 5,070,171 | | 12/1991 | O'Lenick . | |
| 5,099,051 | * | 3/1992 | Beck et al. | 556/405 X |
| 5,481,015 | * | 1/1996 | Nomura | 556/405 |
| 5,627,296 | * | 5/1997 | Dauth et al. | 556/405 |
| 5,872,272 | * | 2/1999 | Yano et al. | 556/405 X |

* cited by examiner

Primary Examiner—Paul F. Shaver

(57) ABSTRACT

The present invention relates to a (a) novel silicone phosphate ester, (b) a method for preparation of said phosphate ester and (c) application of said phosphate ester in industrial and personal care applications.

The compounds of the present invention are made by reacting certain epoxy containing silicone compounds and a salt of an alkyl phosphate ester under aqueous conditions. The resulting compound is quite stable and offers excellent emulsification properties.

15 Claims, No Drawings

SILICONE ALKYL PHOSPHATE ESTERS

BACKGROUND OF THE INVENTION

(1) Field of Invention

The present invention relates to a (a) novel silicone phosphate ester, (b) a method for preparation of said phosphate ester and (c) application of said phosphate ester in industrial and personal care applications.

The compounds of the present invention are made by reacting certain epoxy containing silicone compounds and a salt of an alkyl phosphate ester under aqueous conditions. The resulting compound is quite stable and offers excellent emulsification properties. In addition, compounds of the present invention may also contain a pendant hydroxyl group which alters the water solubility and emulsification properties of the compound. In a preferred embodiment the hydroxy containing group may also contain a polyoxyethylene group and a polyoxypropylene group. The ability to regulate the type of polyoxylakylene group and amount present in the silicone polymer results in a series of products ranging widely in water/oil solubility. The technology used to produce the compounds of the present invention is very flexible and allows us to prepare performance tailored molecules for specific applications.

(2) Object of the Invention

It is the object of the present invention to provide novel a process for the preparation of stable emulsions and microemulsions of oils in water using as an emulsifier a series of novel phosphated silicone polymers.

(3) Description of the Arts and Practices

U.S. Pat. No. 5,070,171, incorporated herein by reference, to O'Lenick, Jr. discloses the preparation dimethicone copolyol phosphates. The compounds of this technology are prepared by reacting a hydroxy containing silicone with a phosphating reagent. While the products are interesting there are several drawbacks. Firstly, there is no way to provide for an alkyl group on the phosphate. Secondly, we have discovered that there is functional improvement to be had by having a free hydroxyl group present in the molecule. This group improves wetting and emulsification. '171 provides for phosphation of all hydroxyl groups. If one were to try to phosphate only some of the hydroxyl groups, there is no way to predict which will phosphate and which will not. This is because all of the hydroxyl groups have identical reactivity.

The Invention

SUMMARY OF THE INVENTION

The compounds of the present invention are made by reacting certain epoxy containing silicone compounds and a salt of an alkyl phosphate ester under aqueous conditions. The resulting compound is quite stable and offers excellent emulsification properties. In addition, compounds of the present invention may also contain a pendant hydroxyl group which alters the water solubility and emulsification properties of the compound. In a preferred embodiment the hydroxy containing group may also contain a polyoxyethylene group and a polyoxypropylene group. The ability to regulate the type of polyoxylakylene group and amount present in the silicone polymer results in a series of products ranging widely in water/oil solubility. The technology used to produce the compounds of the present invention is very flexible and allows us to prepare performance tailored molecules for specific applications.

DETAILED DESCRIPTION OF THE INVENTION

The compounds of the present invention have several key portions in the molecule. Those groups include (a) an alkyl phosphate group, (b) a hydroxy propyl linkage group to silicone polymer, and (c) a silicone polymer that contains water soluble polyoxyalkylene groups. These groups and their positioning in the molecule result in unique properties for the molecule. These include emulsification properties, wetting properties, particularly for hydrophobic pigments, and a lubricious skin feel. This combination of properties has heretofore been unattainable in one molecule.

Compounds of the invention conform to the following structure:

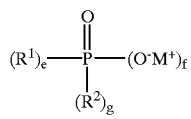

wherein;

$R^1$ is: $CH_3(CH_2)_s$—O—$(CH_2CH_2$—O$)_z$—$(CH_2CH(CH_3)O)_y$—$(CH2CH2-O)x-$; s is an integer ranging from 3 to 21;

$R^2$ is:

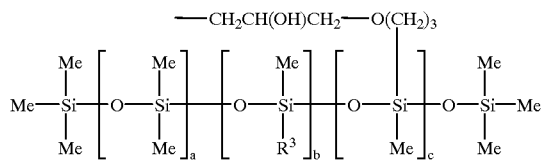

Me is methyl;

a is an integer from 0 to 200;

b is an integer from 0 to 200;

c is an integer from 1 to 200;

$R^3$ is —$(CH_2)_3$—$(OCH_2CH_2)_i$—$(OCH_2CH(CH_3))_j$—$(OCH_2CH_2)_k$—OH;

x, y and z are integers and are independently ranging from 0 to 20;

i, j and k are integers and are independently ranging from 0 to 20;

g ranges from 1 to 3;

e and f range from 0 to 2 with the proviso that e+f+g=3;

M is selected from the group consisting of H, Na, K, Li, and $NH_4$.

Illustrative of the sequence for the preparation of the compounds of the present is as follows;

In a 30% aqueous solution the disodium salt of a phosphate ester (pH 10.4) is reacted with an epoxy dimethicone copolyol to produce the phosphate ester of the present invention:

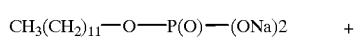 +

-continued

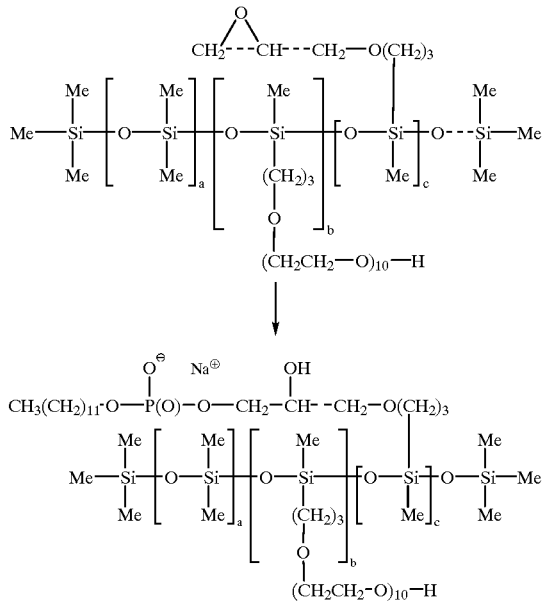

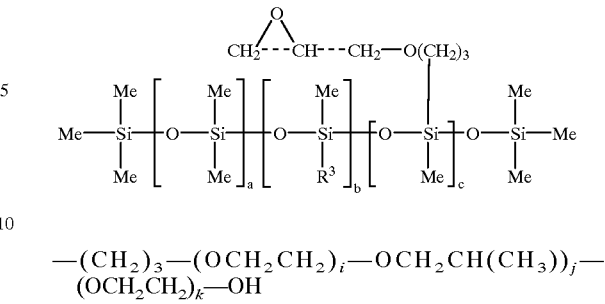

$-(CH_2)_3-(OCH_2CH_2)_i-OCH_2CH(CH_3))_j-(OCH_2CH_2)_k-OH$

| Example | a | b | c | i | j | k |
|---------|-----|-----|-----|----|----|----|
| 1 | 0 | 4 | 1 | 10 | 1 | 0 |
| 2 | 5 | 0 | 5 | — | — | — |
| 3 | 20 | 1 | 10 | 16 | 4 | 10 |
| 4 | 25 | 5 | 50 | 9 | 5 | 10 |
| 5 | 100 | 20 | 100 | 20 | 20 | 20 |
| 6 | 200 | 200 | 200 | 0 | 0 | 0 |

The compounds of the present invention are very good ingredients in a variety of applications that require the presence of both the phosphate and hydroxy group. These applications include:

(a) emulsion polymerization;

(b) urethane foams as modifiers of bubble structure;

(c) pigment dispersion agents for hydrophobic pigments;

(d) personal care applications for excellent skin feel.

Preferred Embodiments

In a preferred embodiment s is 11.

In a preferred embodiment s is 13.

In a preferred embodiments is 16.

In a preferred embodiment x, y, and z are each zero.

In a preferred embodiment x ranges from 3 to 10.

In a preferred embodiment y ranges from 1 to 10.

In a preferred embodiment i, j and k are each zero.

In a preferred embodiment i ranges from 3 to 10.

In a preferred embodiment s is 11 and x ranges from 3 to 10.

In a preferred embodiment s is 13 and x ranges from 3 to 10.

In a preferred embodiment s is 15 and x ranges from 3 to 10.

In a preferred embodiment s is 11 and i ranges from 3 to 10.

In a preferred embodiment s is 13 and i ranges from 3 to 10.

In a preferred embodiment s is 15 and i ranges from 3 to 10.

EXAMPLES

Raw Materials

Silicone Compounds

The silicone compounds useful as intermediates for the preparation of the compounds present invention are commercially available from Siltech LLC, Dacula Ga.

Phosphate Esters

The phosphate esters useful as intermediates for the preparation of the compounds present invention are commercially available from Siltech LLC, Dacula Ga.

They conform to the following structure:

$CH_3(CH_2)_s-O(CH_2CH_2-O)_x-(CH_2CH(CH_3)O)_y-$
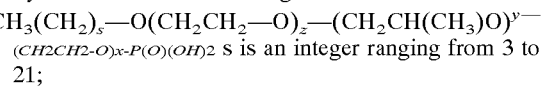 s is an integer ranging from 3 to 21;

x, y and z are integers and are independently ranging from 0 to 20.

| Example | s | x | y | z |
|---------|----|----|----|----|
| 7 | 3 | 0 | 0 | 0 |
| 8 | 5 | 10 | 1 | 20 |
| 9 | 9 | 15 | 20 | 5 |
| 10 | 11 | 20 | 3 | 10 |
| 11 | 17 | 20 | 20 | 20 |
| 12 | 21 | 1 | 10 | 20 |

Preparation of the Products of the Present Invention

General Procedure

Into a suitable vessel equipped with thermometer, agitation and heating capabilities is added the specified amount of water. Next the specified amount of phosphate ester is added under good agitation. The pH is adjusted to 10.3 with the specified base. The reaction mass is heated to 70–80° C. and epoxy silicone is added over 1 hour. The exotherm is watched so that the temperature does not exceed 95° C. If that temperature is reached, cooling is applied and the addition suspended.

After the addition is complete the reaction mass is held at between 80–90° C. for four hours. During that time the % epoxide becomes vanishingly low.

EXAMPLES 13–24

Example 13

Into a suitable vessel equipped with thermometer, agitation and heating capabilities is added grams of water. Next add grams of phosphate ester (Example 7) under good agitation. The pH is adjusted to 10.3 with the KOH. The reaction mass is heated to 70–80° C. Next add grams of epoxy silicone (example 1). Addition is made over a 1 hour time period. The exotherm is watched so that the temperature does not exceed 95° C.

After the addition is complete the reaction mass is held at between 80–90° C. for four hours. During that time the % epoxide becomes vanishingly low.

EXAMPLE 14–24

Example 13 is repeated, only this time the specified amount of water is added, and the specified quantity and type of silicone epoxide and phosphate ester are added replacing the quantity and type in example 13.

| | Silicone Epoxide | | Phosphate Ester | | Water | Base |
|---|---|---|---|---|---|---|
| Example | Example | Grams | Example | Grams | Grams | Type |
| 13 | 1 | 2639.0 | 7 | 171.0 | 3372.0 | KOH |
| 14 | 2 | 249.0 | 8 | 1578.0 | 2193.0 | KOH |
| 15 | 3 | 386.0 | 9 | 2315.0 | 3241.0 | KOH |
| 16 | 4 | 340.0 | 10 | 1780.0 | 2545.0 | KOH |
| 17 | 5 | 4314.0 | 11 | 3307.0 | 9145.0 | NaOH |
| 18 | 6 | 372.0 | 12 | 2567.0 | 3527.0 | NaOH |
| 19 | 1 | 2639.0 | 12 | 2567.0 | 6250.0 | NaOH |
| 20 | 2 | 249.0 | 11 | 3307.0 | 4300.0 | KOH |
| 21 | 3 | 386.0 | 10 | 1780.0 | 3200.0 | LiOH |
| 22 | 4 | 340.0 | 9 | 2315.0 | 3900.0 | KOH |
| 23 | 5 | 4314.0 | 8 | 1578.0 | 7530.0 | NH$_4$OH |
| 24 | 6 | 372.0 | 7 | 171.0 | 750.0 | KOH |

The compounds of the present invention are in aqueous solution or emulsion and generally range from 20–60% solids. The preferred range is 30–40% solids. The products are used without purification.

APPLICATIONS

The products of the present invention are useful in:
(a) Emulsion Polymerization The high molecular weight, the presence of the alkyl substituted anionic group, the presence of silicone group result in the formation of very tight emulsions with very uniform particle size. In addition, the compounds are used at very low concentrations compared to traditional surfactants, resulting in less water blush. A problem well known to those skilled in the emulsion polymer art.

(b) Urethane Foams as Modifiers of Bubble Structure

Traditional dimethicone copolyol compounds have been used in urethane foam. However, the ability to control the water soluble groups and the hydroxyl containing groups independently from each other has been lacking. The compounds of the present invention have polyoxyalkylene groups present in two different and independent groups. This allows for the ability to taylor products that have the desired balance of polyoxyethylene groups, polyoxypropylene groups, hydroxyl groups and phosphate groups independently from each other.

(c) Pigment Dispersion Agents for Hydrophobic Pigments

The ability to control the amount of silicone content in the molecule, as well as the ratio of phosphate to the water soluble groups allows precise regulation of the structure and precise functionality in the dispersion of pigments like TiO$_2$.

(d) Personal Care Applications for Excellent Skin Feel

The products of the present invention have a very lubricious feel on the skin. They are high molecular weight, consequently do not penetrate the skin, causing sting and irritation. Finally, the compounds have an alkyl phosphate group linked through a hydroxy linking group to a silicone. These materials find applications in the formation of liquid crystals and liposomes in personal care applications.

What is claimed:

1. A silicone phosphate conforming to the following structure:

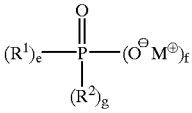

wherein;

R$^1$ is:
CH$_3$(CH$_2$)$_s$—O—(CH$_2$CH$_2$—O)$_z$—(CH$_2$CH(CH$_3$)O)$^y$—(CH2CH2-O)x-;

s is an integer ranging from 3 to 21;

R$^2$ is:

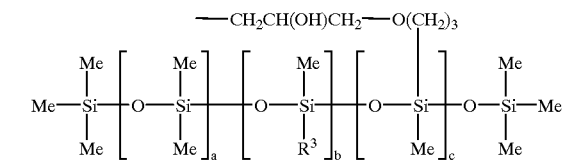

Me is methyl;

a is an integer from 0 to 200;

b is an integer from 0 to 200;

C is an integer from 1 to 200;

R$^3$ is —(CH$_2$)$_3$—(OCH$_2$CH$_2$)$_i$—(OCH$_2$CH(CH$_3$))$_j$—(OCH$_2$CH$_2$)$_k$—OH;

x, y and z are integers and are independently ranging from 0 to 20 ;

i, j and k are integers and are independently ranging from 0 to 20 g ranges from 1 to 3;

e and f range from 0 to 2 with the proviso that e+f+g=3;

M is selected from the group consisting of H, Na, K, Li, and NH$_4$.

2. A silicone phosphate of claim 1 wherein s is 11.
3. A silicone phosphate of claim 1 wherein s is 13.
4. A silicone phosphate of claim 1 wherein s is 10.
5. A silicone phosphate of claim 1 wherein x, y, and z are each zero.
6. A silicone phosphate of claim 1 wherein x ranges from 3 to 10.
7. A silicone phosphate of claim 1 wherein y ranges from 1 to 10.
8. A silicone phosphate of claim 1 wherein i, j and k are each zero.
9. A silicone phosphate of claim 1 wherein i ranges from 3 to 10.
10. A silicone phosphate of claim 6 wherein s is 11.
11. A silicone phosphate of claim 6 wherein s is 13.
12. A silicone phosphate of claim 6 wherein s is 10.
13. A silicone phosphate of claim 9 wherein s is 11.
14. A silicone phosphate of claim 9 wherein s is 13.
15. A silicone phosphate of claim 9 wherein s is 10.

* * * * *